United States Patent [19]

Black et al.

[11] 4,200,103
[45] Apr. 29, 1980

[54] INCREASING ABSORBENT CAPACITY OF SANITARY NAPKIN BY SEALING COVER MATERIAL TO REPELLENT BARRIER

[75] Inventors: Adam R. Black, Red Bank, N.J.; James J. Timlin, New York, N.Y.

[73] Assignee: Personal Products Company, Milltown, N.J.

[21] Appl. No.: 901,178

[22] Filed: Apr. 28, 1978

[51] Int. Cl.$^2$ .............................................. A61F 13/16
[52] U.S. Cl. .................................................. 128/290 W
[58] Field of Search ................ 128/284, 287, 290, 296

[56] References Cited

U.S. PATENT DOCUMENTS

| | | | |
|---|---|---|---|
| 2,896,626 | 7/1959 | Voigtman | 128/287 |
| 3,067,747 | 12/1962 | Wolterding et al. | 128/290 R |
| 3,485,705 | 12/1969 | Harmon | 128/290 W |
| 3,665,921 | 5/1972 | Stumpf | 128/287 |
| 3,888,254 | 6/1975 | Hendricks | 128/290 R |
| 3,913,579 | 10/1975 | Srinivasan et al. | 128/290 R |
| 4,015,604 | 4/1977 | Csillag | 128/290 R |
| 4,026,291 | 5/1977 | Nagano et al. | 128/287 |

Primary Examiner—Robert W. Michell
Assistant Examiner—C. F. Rosenbaum
Attorney, Agent, or Firm—Jason Lipow

[57] ABSTRACT

An improvement is provided in a absorbent product for absorbing and retaining body fluids of the kind having a body facing side and a garment facing side and comprising an elongated, planar absorbent pad. The pad is enveloped in a generally rectangular menstrual fluid pervious wrapper with the longitudinal edges of the wrapper overlapping on the garment facing side of the product. A generally rectangular menstrual fluid impervious barrier sheet is sandwiched between the wrapper and the pad. The barrier sheet overlies the garment facing side of the pad and at least the longitudinal side edges of the pad. At least two menstrual fluid barrier seal lines are provided extending longitudinally with the product and sealing the longitudinal edge portions of the barrier sheet to the cover. The seals will prevent menstrual fluid from transferring, either by wicking or by seeping, across the seal line, thereby insuring that the garment facing side of the napkin is free of menstrual fluid.

6 Claims, 5 Drawing Figures

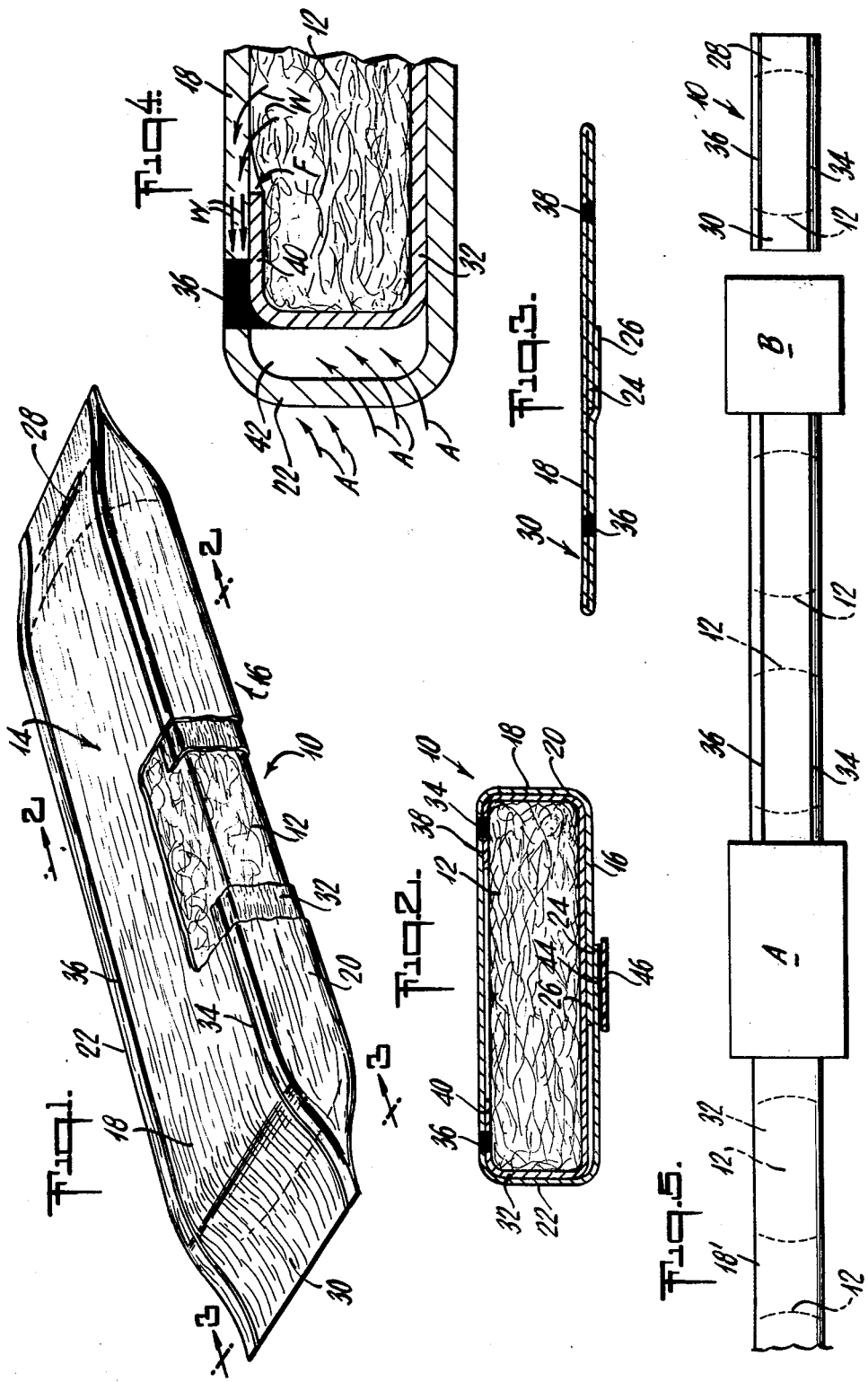

INCREASING ABSORBENT CAPACITY OF SANITARY NAPKIN BY SEALING COVER MATERIAL TO REPELLENT BARRIER

BACKGROUND OF THE INVENTION

This invention relates to absorbent products and more particularly to products used for absorbing and retaining body fluids and worn in contact with the body such as diapers, sanitary napkins, dressings and the like.

In general, such products comprise one or more layers of a core of hydrophylic material such as wood pulp, rayon, gauze, tissue or the like and in some cases, synthetic hydrophilic material such as hydrophilic polyurethane foam. The hydrophilic material is generally provided in the form of a pad, usually having a rectangular shape and enveloped in a cover which can be a woven material such as gauze or a non-woven fabric. The cover is pervious to body fluids on at least the side of the product designed to be placed against the body. A body fluid impervious barrier sheet is generally provided on the opposite side of the pad, i.e., the side facing away from the body, in an effort to protect the clothing from staining and wetting.

The absorbent product is positioned on the body so that the body fluid being absorbed strikes the pad in a central area thereof and ideally, should then be evenly distributed by wicking action throughout the entire pad. The ideal situation of even distribution will make maximum use of the absorbent material in the product and thus, in theory, the outer surfaces will not be wet and the pad will not require changing until all of the absorbent material is saturated.

Unfortunately, the real situation is far from this ideal. In practice, fluid striking a major surface of a rectangular pad is first absorbed into the pad for a certain distance and then wicks radially in all directions. Since the width of the rectangular pad is less than its length, fluid wicking radially first wets an outer surface at the longitudinally extending side edges of the product. While this occurs long before the entire pad is totally saturated, once the edges of the product are wet, it is necessary to change the product even though only a small portion of the potential absorption capacity has been utilized.

Those skilled in the art, therefore, have directed their efforts toward solving this side leakage problem. One solution, employed with such products as disposable diapers and sanitary napkins, is to provide an impervious barrier sheet on the side of the pad facing away from the body, this sheet being sized wider than the pad, i.e., extending beyond the pad along each longitudinal edge. The wide edges are then folded to cover the longitudinally extending side edges of the pad and preclude the passage of fluid therethrough. Unfortunately, this construction imparts undesirable effects when the barrier sheet, normally a polymeric film, is placed against or in juxtaposition with the skin of the user for a significant length of time. This is due to the inherent nature of most commercially employed barrier sheets, e.g., polyethylene, which have extremely poor moisture vapor and gas transmission properties so that, in the areas where they contact the skin, they substantially inhibit moisture vapor transmission, thereby retaining moisture in contact with the skin and leading to irritation and the formation of rashes, etc.

An attempted improvement is described in U.S. Pat. No. 3,230,955 issued on Jan. 25, 1966 to C. G. Joa et al. wherein a barrier sheet is sandwiched between two layers of cellulosic material and then employed to cover the side of the pad facing away from the body and the longitudinal sides of the pad. Another cover is applied to fully overwrap the product. While the layers of cellulosic material and the overwrap do add to the comfort of the product, they do so by decreasing the effectiveness of the barrier sheet in preventing side leakage. This is because the cellulosic layer and the wrapping, having a high wicking rate for fluids, tend to transfer body fluids which wet the body facing side of the pad to the longitudinal sides of the pad thus frustrating the purpose of the barrier sheet.

The problem of side leakage and the concomitant problem of user comfort has also been addressed in U.S. Pat. No. 4,015,604 issued on Apr. 5, 1977 to Charles Csillag. In accordance with this disclosure, the longitudinal edges of the pad are impregnated with a hydrophobic material to create hydrophobic zones which retard fluid transmission to the outer edges of the pad. Buffer zones between the extreme longitudinal edges of the pad and the hydrophobic zones are provided to insure user comfort. While a product made in accordance with this patent functions well, certain drawbacks are associated therewith. Firstly, the application of the hydrophobic zones is a difficult and expensive processing step and adds significantly to the manufacturing costs of the product. Secondly, the requirement of buffer zones and hydrophobic zones subtract from the useful absorbent portion of the pad and hence reduce to a degree the overall efficient use of the absorbent material of the pad.

In view of the above-described shortcomings of the prior art, a need still exists for a product which alleviates the side leakage problem while still being comfortable in use.

SUMMARY OF THE INVENTION

It has now been discovered that an absorbent product can be provided which solves the problem of side leakage without introducing the concomitant problem of skin irritation, which can be manufactured with essentially no incremental cost increase, and will not reduce the usable absorbent capacity of the product.

Specifically, there has been provided an improvement in an absorbent product for absorbing and retaining body fluids of the kind having a body facing side and a garment facing side and comprising an elongated, planar absorbent pad. The pad is enveloped in a generally rectangular menstrual fluid pervious wrapper with the longitudinal edges of the wrapper overlapping on the garment facing side of the product. A generally rectangular menstrual fluid impervious barrier sheet is sandwiched between the wrapper and the pad. The barrier sheet overlies the garment facing side of the pad and at least the longitudinal side edges of the pad.

In accordance with the teachings of this invention, at least two menstrual fluid barrier seal lines are provided extending longitudinally with the product and sealing the longitudinal edge portions of the barrier sheet to the cover. As used herein, the term "menstrual fluid barrier seal line" is meant to apply to any seal line which will adhere the barrier sheet to the wrapper and which will prevent menstrual fluid from transferring either by wicking or by seeping across the seal line.

Several distinct advantages accrue from the above described construction. Firstly, the primary object of precluding menstrual fluid from emerging on the external side edges of the product is accomplished. In fact, the entire portion of the external area of the product consisting of the two longitudinal sides and the garment facing side of the product and included between the two menstrual barrier seal lines will be free of leakage. The simple expedient of sealing the barrier sheet to the wrapper in this manner precludes menstrual fluid from either seeping between the barrier sheet and wrapper and then onto the longitudinal sides of the product or alternatively, from transferring to the longitudinal sides by the wicking action of the wrapper.

Further, the product is comfortable in use in that the wrapper provides a soft comfortable interface between the barrier sheet and the skin of the user. Still another important advantage accrues from the construction of this invention. The wrapper is adhered to the barrier sheet only at the two menstrual barrier seal points. Accordingly a dry, menstrual fluid free "pocket" is formed between the seal lines around that portion of the product which includes the garment facing side. Accordingly, if as is preferred, a wrapper is chosen which is gas permeable, air and water vapor can freely move across both the external and internal faces of the wrapper. The importance of this feature is that body moisture, such as for example perspiration, which is deposited on the side of the product can be easily carried away by diffusion and evaporation and will not instead collect and cause the skin irritation as has heretofore been associated with products of this kind.

BRIEF DESCRIPTION OF THE DRAWINGS

In the drawings:

FIG. 1 is a perspective view of a sanitary napkin embodying the teachings of this invention;

FIG. 2 is a cross-sectional view of the napkin of FIG. 1 taken through line 2—2;

FIG. 3 is a cross-sectional view of the tab of the napkin of FIG. 1 taken through line 3—3;

FIG. 4 is a schematic enlarged cross-sectional view of the longitudinal edge portion of the napkin of FIGS. 1 and 2; and FIG. 5 is a schematic planar view of a part of a production line for manufacturing the product of this invention.

DETAILED DESCRIPTION OF THE INVENTION

Referring now to FIGS. 1-3 of the drawings, illustrated therein in perspective and cross-sectional views is a sanitary napkin 10 embodying the teachings of this invention. The napkin is generally planar, having two major surfaces one of which is to be applied against the body of the user and herein designated the body facing side 14. The opposite major surface, normally applied against the undergarment of the user, is herein designated the garment facing side 16.

The napkin consists of an absorbent element 12 which is shown in the form of an elongated planar absorbent pad and may consist of loosely associated absorbent hydrophilic material such as cellulosic fibers, e.g., wood pulp, regenerated cellulose or cotton fibers; other chemically or physically modified cellulosic fibers; other polymeric absorbent materials, both natural and synthetic, such as hydrophilic foams (e.g., hydrophilic polyurethane foam); or may be such commonly used absorbent material as wadded tissue paper or the like. Alternatively, the absorbent element 12 may be a shaped form such as molded hydrophilic polymer (e.g., a molded hydrophilic polyurethane foam or a molded cellulosic foam) or any combination of these or similar absorbent materials.

A menstrual fluid pervious wrapper 18 envelopes the body facing side 14, the garment facing side 16 and the longitudinal sides 20 and 22 of the napkin. Generally, the wrapper is a single rectangular sheet of material having a width sufficient to encircle the absorbent element 12 and having the longitudinal side edges 24 and 26 overlap and be sealed together on the garment facing side 16 of the napkin. Preferably the wrapper 18 is longer than the absorbent element 12 so as to form end tabs 28 and 30, which may be sealed to fully enclose the element 12. The wrapper 18 may be any woven or nonwoven material pervious to body fluid striking its surface, such covers being well-known in the art and usually comprising cellulosic materials such as cotton, rayon or wood pulp. As will be more fully discussed herein, in one embodiment of this invention it is preferable that the wrapper comprise fibers of filaments of thermoplastic polymers such as polyethylene or polypropylene.

Sandwiched between the wrapper 18 and the absorbent element 12 is a menstrual fluid impervious barrier sheet 32 overlying the garment facing side and at least the longitudinal side edges 20 and 22 of the element 12. Preferably, the barrier sheet also overlies the extreme longitudinal marginal portions of the body facing side 14. The barrier sheet is provided to preclude the transfer of any menstrual fluid absorbed by and transferred through the element 12 from reaching the external portion of the napkin in contact with the body or garment of the wearer and, in particular, to prevent the external surfaces of the garment facing side 16 and the longitudinal sides 20 and 22 from becoming wet with menstrual fluid. To accomplish this purpose, the barrier sheet may comprise any thin flexible menstrual fluid impervious material such as, for example, a polymeric film, e.g., polyethylene, polypropylene, cellophane or even an usually fluid pervious material that has been treated to be impervious such as impregnated fluid repellent paper.

In accordance with the teachings of this invention, two menstrual fluid barrier seals 34 and 36 are provided sealing the longitudinal edge portions 38 and 40 of the barrier sheet to the wrapper 18. The seals 34 and 36 extend longitudinally along the full length of the element 18 and preferably extend for the full length of the wrapper 18. By extending the seals 34 and 36 along the full length of the product, as best viewed in FIG. 3, these same seals either alone or in conjunction with additional seals, may be used to close the tab ends 28 and 30 of the product.

Several methods may be employed for effecting the seals provided, of course, that the method chosen results in a seal between the barrier sheet and the wrapper which inhibits the transfer of menstrual fluid, either by wicking or diffusion. For example, the seal may be effected by employing a mensophobic (and generally hydrophobic) adhesive material, i.e., by extruding onto the surface of the wrapper overlying the edge portions 38 and 40 a flowable emulsion or solution of such adhesive which will impregnate through the thin pervious wrapper and adhere the same to the barrier film. The impregnation process can be aided by the application of pressure along the extruded line. Alternatively, a line of adhesive may be deposited on the barrier sheet before the wrapper is applied. After application of the wrapper, the two layers may be sealed together upon application of pressure. Examples of emulsion-type adhesive suitable for this purpose are emulsions of polyvinyl acetate, acrylicpolymers and copolymers styrene-budadiene adhesives which may be dispersed for example in a continuous phrase of water. Also suitable for this purpose are the so-called "hot melt" adhesives which when heated can likewise be extruded onto the product in a manner similar to the adhesive referred to above. Examples of suitable hot-melt adhesives are based on polymers such as polyacrylamide, thermoplastic rubbers and ethylenevinyl acetate copolymers.

In a preferred embodiment the wrapper 18 is chosen to contain fibers or filaments of thermoplastic polymeric material such as the polyolefins, e.g., polyethylene and polypropylene. When used in conjunction with a barrier sheet comprised of similar thermoplastic materials, the seals 34 and 36 may be accomplished simply by the application of heat and pressure, i.e., by heat sealing.

As best viewed in FIG. 2, the menstrual fluid barrier seals 28 and 30, in combination with the barrier sheet 32 and the wrapper 18 form a menstrual fluid-free "pocket" 42 which surrounds the portion of the product lying between the two seals and including the longitudinal side edges 20 and 22 and the garment facing side 16 of the product. As will be more fully described herein after, this pocket 42 insures user comfort and avoids the skin irritation heretofore associated with products of this kind.

The embodiment of this invention illustrated in FIGS. 1-3 depicts a sanitary napkin of the kind which is held in place by adhesion to the crotch portion of an undergarment. Accordingly, the garment facing side of the napkin is provided with a strip 44 of pressure sensitive adhesive applied centrally and longitudinally for adherence to the undergarment. A protective cover 46 is provided to overlie the adhesive strip 44 and may be peelably removed just prior to use. It will be understood by those skilled in the art that the invention is not limited to adhesively attached napkins and that the teachings herein apply equally to napkins held in place by any of the means well known in the art as, for example, with pins, belts or the like. In these cases, the tab ends 30 and 28 may be elongated to accommodate such pins or belts, this elongation being accomplished by using a longer sheet of wrapping material.

The advantages of the invention are more fully understood by reference to FIG. 4 which is an enlarged, somewhat schematic cross-sectional view of one longitudinal side of the sanitary napkin depicted in FIGS. 1-3. For the purpose of this FIG. 4, it is assumed that the absorbent element 12 has absorbed and retained substantial quantities of menstrual fluid. Accordingly, the body facing side 14 of the napkin is now wet at least in its central portions with menstrual fluid and, if the wrapper 18 is constructed of a wettable material such as a non-woven material of cellulose fibers, menstrual fluid will transfer by wicking toward the longitudinal sides of the napkin (illustrated in the drawings by the arrows labeled W). In accordance with this invention, however, by virtue of the menstrual fluid barrier seal 36, this wicking action is arrested and does not continue onto the longitudinal side 22. Additionally, there is a tendency for menstrual fluid to seep between the wrapper 18 and the barrier sheet 32 (this seepage being illustrated by the arrow labeled F). Again, the menstrual fluid barrier seal 36 of this invention precludes such menstrual fluid transfer, leaving the longitudinal side 22 of the product dry. Further, because the longitudinal side 22 is generally worn against the skin of the user, there is a tendency for body fluids such as perspiration to collect on the external surface of the wrapper 18 and then between the wrapper and the barrier sheet. In accordance with the construction taught herein, by virtue of the "pocket" 42 formed between the barrier sheet and the wrapper, this area is open to a free circulation of moisture vapor and air on both the outside and inside surfaces of the wrapper 18 (as depicted by the arrows labeled A) whereby such perspiration can be evaporated and removed from the product before causing user skin irritation.

FIG. 5 illustrates a method of manufacturing the product of this invention. Referring to this figure, shown therein schematically is a planar view of a part of the production line for applying the menstual fluid barrier seals 34 and 36 to the product. A plurality of spaced apart absorbent elements 12, each having a barrier sheet 32 applied as has been described above, are wrapped in a continuous web of wrapper material 18' which is overlapped on the garment facing side (the underside of the product, as depicted in FIG. 5). This assembly passed by conveyor means (not shown) under two stations: sealing station A and cutting station B. Sealing station A effects the two continuous, longitudinal seals 34 and 36 of this invention. When the sealing is effected by adhesive, station A may be an adhesive extruder which may also include means for applying sealing pressure. When the sealing is effected by heat sealing, station A may be a heat sealer. At cutting station B, the continuous web 18' is cut at the spaces between elements 12 to form the individual products, the spaces providing the tabs 28 and 30 of the product.

The advantages of the instant invention can be better understood by reference to the following Example.

EXAMPLE

A first series of sanitary napkins, each having the configuration of those shown in FIGS. 1-3, is prepared. The napkins have overall rectangular dimensions of 9.5 inches by 2.7 inches and are 0.5 inches thick. The absorbent element is a rectangualr pad of comminuted wood pulp having the overall dimensions of 7.5 by 2.7 by 0.5 inches and weighing 6 grams. The garment facing side and longitudinal side of the element as well as 0.15 inches of the extreme longitudinal portions of the body facing side are wrapped in a rectangular barrier sheet of polyethylene film having the overall dimension of 4.0 by 9.5 inches and being 0.5 mils thick. A wrapper of 100% polyester fiber envelops the product. Two menstrual fluid barrier seals are provided on the body facing side of the napkin each 0.10 inch from the longitudinal edge and each 3/32 inch in width and extending along the full longitudinal length of the napkin. The seals are effected by extruding onto the surface of the wrapper a line of Bostik 4309 adhesive which is a hot melt of ethylene vinyl acetate (eva) and is available from the Bostik Division of USM Corp.

A second series of napkins are prepared, identical in all respects to the first series with the exception that the menstrual fluid barrier seals are omitted.

Both series of napkins are tested in a Dynamic Form test in which a napkin is adhered to a rubber mold which simulates the female form. The napkin is held in place using commercially available panty hose. The form is set into motion by means of a set of gears, cams and rods to simulate a walking motion and an ersatz menstrual fluid containing one percent NaCl, by weight, is allowed to drip onto the napkin. The fluid is applied at a rate of 3.4 c.c. per minute and the form is operated at a speed of 60 cycles per minute. The end point of the test is determined by noting when fluid wets the longitudinal sides of the product, at which point, the total quantity of fluid absorbed by the napkin is recorded as the napkin capacity.

Table I summarizes the results obtained by testing the two series of napkins:

TABLE I

| SAMPLES | NO. OF SAMPLES | AVERAGE ABSORBENT CAPACITY (c.c.) |
| --- | --- | --- |
| With seals | 10 | 51.5 |
| Without seals | 10 | 33.1 |

In each case described above, the napkin failure occured because of side leakage. As the data clearly indicates, the napkins embodying the teaching of this invention exhibited a more than 55% increase in capacity prior to failing.

It will be understood by those skilled in the art that the above-described embodiment of this invention is merely illustrative and many variations are possible while still remaining within the scope of this invention. For example, the menstrual fluid barrier seal lines need not be limited to a single pair of lines but instead, multiple pairs of lines could be employed. Other variations will occur to those skilled in the art.

What is claimed is:

1. A sanitary napkin having a body facing side and a garment facing side and comprising:

an elongated, planar absorbent pad;

a generally rectangular menstrual fluid pervious wrapper enveloping said pad, the longitudinal edges of said wrapper extending longitudinally and overlapping on the garment facing side of the napkin;

a generally rectangualr menstrual fluid impervious barrier sheet having longitudinal edges and being sandwiched between said wrapper and said pad, said barrier sheet extending longitudinally with said pad and overlying said garment facing side of said pad, the longitudinal side edges of said pad, and the extreme longitudinal marginal portions of the body facing side; and at least two menstrual fluid barrier seal lines extending longitudinally with said pad on said body facing side sealing the longitudinal edge portions of said barrier sheet to said wrapper, whereby menstrual fluid is inhibited from transferring from said pad to the area between said wrapper and said barrier sheet.

2. The napkin of claim 1 wherein the menstrual fluid barrier seal lines comprise mensophobic adhesive.

3. The napkin of claim 2 wherein the menstrual fluid barrier seal lines extend along the full longitudinal length of the wrapper thereby sealing said end tabs.

4. The napkin of claim 1 wherein the menstrual fluid pervious wrapper comprises thermoplastic polymeric material.

5. The napkin of claim 4 wherein the menstrual fluid barrier seal line is a heat seal.

6. The napkin of claim 1 wherein the wrapper is longer than the pad to form end tabs.

* * * * *